United States Patent
O'Lenick, Jr. et al.

(10) Patent No.: US 6,461,598 B1
(45) Date of Patent: Oct. 8, 2002

(54) PROCESS FOR CONDITIONING HAIR

(75) Inventors: Anthony J. O'Lenick, Jr., Dacula, GA (US); Charles W. Buffa, Paterson, NJ (US); Kevin A. O'Lenick, Dacula, GA (US)

(73) Assignee: Biosil Research Institute Inc., Paterson, NJ (US)

( * ) Notice: Subject to any disclaimer, the term of this patent is extended or adjusted under 35 U.S.C. 154(b) by 0 days.

(21) Appl. No.: 09/916,820

(22) Filed: Jul. 27, 2001

Related U.S. Application Data

(63) Continuation-in-part of application No. 09/483,899, filed on Jan. 11, 2000.

(51) Int. Cl.[7] ................................................. A61K 7/06
(52) U.S. Cl. .................. 424/70.1; 424/401; 424/70.11; 514/880; 560/89; 560/198
(58) Field of Search ................................. 424/401, 70.1, 424/70.11; 514/880; 560/89, 198

(56) References Cited

U.S. PATENT DOCUMENTS 5,300,287 A * 4/1994 Park ........................ 424/78.04
6,372,934 B1 * 4/2002 O'Lenick et al. ........... 560/198

FOREIGN PATENT DOCUMENTS

| JP | 130 509 | * 10/1979 |
| JP | 0 580 435 A1 | * 1/1994 |
| WO | WO 96/36871 | * 11/1996 |

* cited by examiner

Primary Examiner—Jose' G. Dees
Assistant Examiner—Konata M. George

(57) ABSTRACT

The invention relates to a process for conditioning and cleaning hair, which comprises contacting the hair with an effective conditioning amount of a series of novel salt complexes. These complexes provide outstanding conditioning effects to the hair and are very mild to the eye. The complexes are made by neutralizing a fatty ammonium compound that is cationic with an anionic compound, producing a salt complex. Optionally, the complex can be combined with dimethicone copolyol to produce extremely mild products suitable for use in shampoos, body washes, and cleanser. The mildness makes these compounds of particular interest in baby shampoos.

19 Claims, No Drawings

PROCESS FOR CONDITIONING HAIR

RELATED APPLICATION

This application is a continuation in part of co-pending Ser. No. 09/483,899 filed Jan. 11, 2000.

BACKGROUND OF THE INVENTION

1. Field of the Invention

The invention relates to a process for conditioning and cleaning hair which comprises contacting the hair with an effective conditioning amount of a series of novel salt complexes. These complexes provide outstanding conditioning effects to the hair and are very mild to the eye. The complexes are made by neutralizing a fatty ammonium compound that is cationic with an anionic compound, producing a salt complex. Optionally, the complex can be combined with dimethicone copolyol to produce extremely mild products suitable for use in baby shampoos. The compounds of the present invention are water soluble, non-irritating to the eye and skin and are well suited to personal care applications.

2. Arts and Practices

Fatty quaternary compounds commonly called quats, are tetrasubstituted ammonium compounds where each of the four groups on nitrogen are a group other than hydrogen. If any hydrogen groups are present, the compounds are not quaternary amines, but rather are primary or secondary amines.

The most commonly encountered substituents are alkyl and alkyl amido groups. There are several classes of quats. The most important are (a) alkyl tri methyl quats for example cetyltrimonium chloride, (b) alkylamidopropyl dimethyl quats like stearylamidalkonium chloride and (c) di alkyl, di methyl quats for example dicetyldimonium chloride and (d) alkyl, benzyl, Di methyl quats like stearalkonium chloride.

There are several undesirable attributes of fatty cationic products.

1. Fatty Quaternary compounds are incompatible with anionic surfactants since an insoluble complex frequently is formed when the two types of materials are combined.

2. Many fatty Quaternary Compounds are eye irritants. The material is minimally irritating to the eyes at concentrations of 2.5%, which limits the concentration which is useful if low irritation is a requirement.

3. Fatty quats are generally hydrophobic and when applied to substrate can cause a loss of absorbance of the substrate. It is not an uncommon situation for a traveler to a hotel to encounter a very soft towel that totally fails to absorb water. This is because the fatty quaternary gives softness but being hydrophobic also prevents re-wet. This situation also can be observed on hair, the conditioner becomes gunky on the hair and has a tendency to build up.

We have learned that many of these negative attributes can be unexpectantly mitigated by making fatty complexes with carboxy fatty alcohol alkoxylates. The preferred complex has to have a molecular weight of over 1000 molecular weight units to obtain the most effective irritation mitigation. The mitigation of irritation, the improved water solubility and the skin feel make the compounds of the present invention highly desirable in personal care applications, Thus the present invention relates to a process for conditioning and cleaning hair which comprises contacting the hair with an effective conditioning amount of said series of novel salt complexes. Optionally, the complex can be combined with dimethicone copolyol to produce extremely mild products suitable for use in baby shampoos. The effective conditioning concentration for the process of the present invention runs between 0.01 and 10.0% by weight of the shampoo. The preferred is 0.2 to 2.0% by weight.

THE INVENTION

OBJECT OF THE INVENTION

It is the object of the present invention to provide a process for conditioning hair which comprises contacting the hair with an effective conditioning amount of a series of novel complexes that are made by neutralizng a fatty ammonium compound which is cationic with an anionic compound, producing a salt complex.

SUMMARY OF THE INVENTION

In a broad sense, the present invention discloses a process for conditioning hair which comprises contacting the hair with an effective conditioning amount of a series of novel complexes that are made by neutralizing a fatty ammonium compound which is cationic with an anionic compound, producing a salt complex. The effective conditioning concentration for the process of the present invention runs between 0.01 and 10.0% by weight of the shampoo. The preferred is 0.2 to 2.0% by weight.

DETAILED DESCRIPTION OF THE INVENTION

The process of the present invention is performed using the compounds conforming to the following structure:

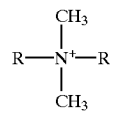

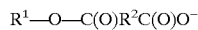

wherein;

$R^1$ is $CH_3-(CH_2)_n-O-(CH_2CH_2O)_a-(CH_2CH(CH_3)O)_b-(CH_2CH_2O)_c-$;

n is an integers ranging from 7 to 21;

a and c are integers independently ranging from 0 to 20, with the proviso that a+b be greater than 5;

b is an integer ranging from 0 to 20;

$R^2$ is selected from the group consisting of

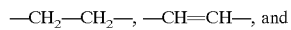

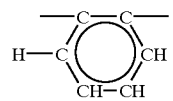

$R^3$ is selected from the group consisting of

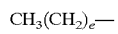

and

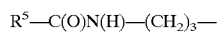

$R^5$ is $CH_3(CH_2)_f$— e is an integer from 5 to 21;

f is an integer from 5 to 21;

$R^4$ is selected from the group consisting of

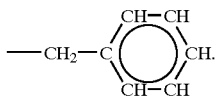

g is an integer ranging from 0 to 21 and

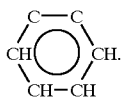

Preferred Embodiments

The effective conditioning concentration for the process of the present invention runs between 0.01 and 10.0% by weight of the shampoo. The preferred is 0.2 to 2.0% by weight.

In a preferred embodiment R is;

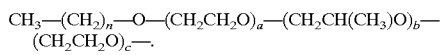

In a preferred embodiment $R^2$ is —$CH_2$—$CH_2$—.

In a preferred embodiment $R^2$ is —CH=CH—.

In a preferred embodiment $R^2$ is

[structure]

In a preferred embodiment e is an integer ranging from 7 to 21.

In a preferred embodiment $R^3$ is $R^5C(O)N(H)$—$(CH_2)_3$— f is an integer ranging from 5 to 21.

In a preferred embodiment $R^4$ is methyl.

In a preferred embodiment $R^4$ is

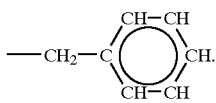

In a preferred embodiment the molecular weight of the complex is greater than 1000.

In another preferred embodiment, the complex is blended with dimethicone copolyol to improve the conditioning effect and feel.

EXAMPLES OF REACTANTS

ANHYDRIDES

The various anhydrides listed are all items of commerce and are prepared by methods known to those skilled in the art.

Reactant Example I (Succinic Anhydride

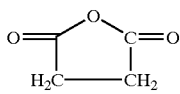

Reactant Example II (Maleic Anhydride)

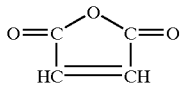

Reactant Example III (Phthalic Anhydride)

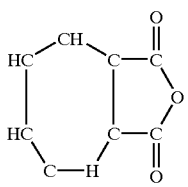

Alcohol Alkoxy Carboxylate

The reaction sequence is illustrated by the reaction with succinic anhydride

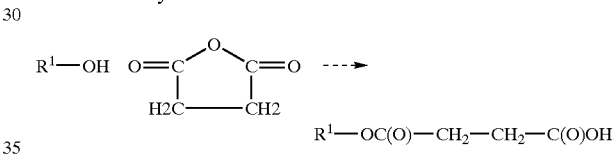

Raw Materials

Alkoxylated alcohols suitable for the preparation of the compounds of the present invention are commercially available from Siltech Corporation in Toronto Ontario Canada.

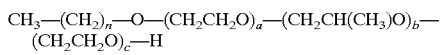

| Example | n | a | b | c |
|---------|----|----|----|----|
| 1 | 8 | 0 | 0 | 5 |
| 2 | 10 | 0 | 1 | 12 |
| 3 | 12 | 20 | 10 | 20 |
| 4 | 14 | 3 | 1 | 3 |
| 5 | 16 | 20 | 20 | 20 |
| 6 | 18 | 12 | 0 | 0 |
| 7 | 20 | 12 | 1 | 1 |
| 8 | 22 | 5 | 0 | 5 |

General Reaction Conditions;

Into a suitable round bottom, three neck flask equipped with a thermometer and a nitrogen sparge is added the specified number of grams of the specified alcohol alkoxylate compound and the specified number of grams of the specified anhydride. The reaction mass is blanketed with nitrogen, and heated to 80 and 110 C under the inert nitrogen blanket. Within four to five hours the theoretical acid value is obtained. The product is a clear liquid and is used without additional purification.

Examples 9–18

Succinic Derivatives

Into a suitable round bottom, three neck flask equipped with a thermometer and a nitrogen sparge is added the specified number of grams of the specified alcohol alkoxylate (examples 1–8) compound and the 100.0 grams of succinic anhydride. The reaction mass is blanketed with nitrogen, and heated to 80 and 110 C under the inert nitrogen blanket. Within four to five hours the theoretical acid value is obtained. The product is a clear liquid and is used without additional purification.

| Example | Alcohol Alkoxylate Example Grams |
|---|---|
| 9 | 1391.0 |
| 10 | 2742.0 |
| 11 | 32533.0 |
| 12 | 4447.0 |
| 13 | 53179.0 |
| 14 | 6795.0 |
| 15 | 7926.0 |
| 16 | 8763.0 |

Examples 17–24

Maleic Derivatives

Into a suitable round bottom, three neck flask equipped with a thermometer and a nitrogen sparge is added the specified number of grams of the specified alcohol alkoxylate (examples 1–8) compound and the 98.0 grams of maleic anhydride. The reaction mass is blanketed with nitrogen, and heated to 80 and 110 C under the inert nitrogen blanket. Within four to five hours the theoretical acid value is obtained. The product is a clear liquid and is used without additional purification.

| | Alcohol Alkoxylate | |
|---|---|---|
| Example | Example | Grams |
| 17 | 1 | 391.0 |
| 18 | 2 | 742.0 |
| 19 | 3 | 2533.0 |
| 20 | 4 | 447.0 |
| 21 | 5 | 3179.0 |
| 22 | 6 | 795.0 |
| 23 | 7 | 926.0 |
| 24 | 8 | 763.0 |

Examples 25–32

Phthalic Derivatives

Into a suitable round bottom, three neck flask equipped with a thermometer and a nitrogen sparge is added the specified number of grams of the specified alcohol alkoxylate (examples 1–8) compound and the 146.0 grams of phthalic anhydride. The reaction mass is blanketed with nitrogen, and heated to 80 and 110 C under the inert nitrogen blanket. Within four to five hours the theoretical acid value is obtained. The product is a clear liquid and is used without additional purification

| | Alcohol Alkoxylate | |
|---|---|---|
| Example | Example | Grams |
| 25 | 1 | 391.0 |
| 26 | 2 | 742.0 |
| 27 | 3 | 2533.0 |
| 28 | 4 | 447.0 |
| 29 | 5 | 3179.0 |
| 30 | 6 | 795.0 |
| 31 | 7 | 926.0 |
| 32 | 8 | 763.0 |

Cationic Examples

The cationic compounds of the present invention are commercially available from a variety of sources including Croda Inc. and Siltech Corporation. They conform to the following structure:

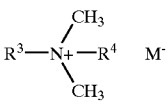

wherein;

$R^3$ is selected from the group consisting of

and

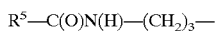

$R^5$ is $CH_3(CH_2)_f-$ e is an integer from 5 to 21;

f is an integer from 5 to 21;

$R^4$ is selected from the group consisting of $CH_3(CH_2)_g$ g is an integer ranging from 0 to 21;

and

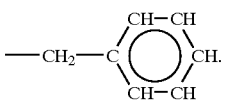

M is selected from the group consisting of $Cl^-$, $Br^-$, and $CH_3SO_4-$.

As used herein

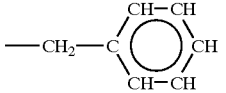

is referred to as benzyl.

Class 1 Cationic Compounds

| Example | e | g |
|---------|----|--------|
| 33 | 7 | 0 |
| 34 | 11 | 0 |
| 35 | 17 | 0 |
| 36 | 17 | 0 |
| 37 | 21 | 0 |
| 38 | 21 | benzyl |

M is Cl$^-$

Class 2 Cationic Compounds

| Example | e | g |
|---------|----|--------|
| 39 | 7 | 7 |
| 40 | 11 | 7 |
| 41 | 15 | 21 |
| 42 | 17 | 3 |
| 43 | 21 | 5 |
| 44 | 17 | benzyl |
| 45 | 21 | benzyl |

M is Cl$^-$

Class 3 Cationic Compounds $R^3$ is $R^5C(O)N(H)-(CH_2)_3-$

| Example | f | g |
|---------|----|--------|
| 46 | 7 | 0 |
| 47 | 9 | 0 |
| 48 | 11 | 0 |
| 59 | 17 | 11 |
| 50 | 21 | 21 |
| 51 | 17 | Benzyl |
| 52 | 5 | 11 |

M is Cl$^-$

Complexation

The carboxy fatty alcohol alkoxylate (examples 9–32) and the cationic compound (examples 33–52) are blended into water to make up a concentration of between 20–70%. The preferred range is 30–50% by weight. The pH of the resulting mixture is then adjusted to between 5 and 9. The lower pH is preferred for skin care products, the higher for hair care products. The complex forms in aqueous solution and the counter ion on the cationic material remains in the solution as inorganic salt.

Example 53 suitable vessel is added 840.0 grams of water. Next 491.0 grams of anionic pound Example 9 is added under agitation Next 209.0 grams of cationic pound 33 is added. The pH is adjusted to 7.0 with KOH. The complex is as prepared.

Examples 54–76

Example 53 is repeated, only this time the specified amount of water. Next the specified amount of the specified anionic compound is added. Next the specified amount of the specified cationic compound is added. The pH is adjusted to 7.0 with KOH. The complex is used as prepared.

Examples 54–76

| Example | Anionic Compound Example | Anionic Compound Grams | Cationic Compound Example | Cationic Compound Grams | Water Grams |
|---------|---------|-------|---------|-------|-------|
| 54 | 10 | 842.0 | 34 | 265.0 | 1328.0 |
| 55 | 11 | 2633.0 | 35 | 349.0 | 3578.0 |
| 56 | 12 | 547.0 | 36 | 373.0 | 1104.0 |
| 57 | 13 | 3279.0 | 37 | 405.0 | 4420.0 |
| 58 | 14 | 895.0 | 38 | 416.0 | 1704.0 |
| 56 | 15 | 1026.0 | 39 | 293.0 | 1582.0 |
| 60 | 16 | 863.0 | 40 | 349.0 | 1515.0 |
| 61 | 17 | 489.0 | 41 | 601.0 | 1635.0 |
| 62 | 18 | 840.0 | 42 | 377.0 | 1292.0 |
| 63 | 19 | 2631.0 | 43 | 416.0 | 3656.0 |
| 64 | 20 | 545.0 | 44 | 389.0 | 1167.0 |
| 65 | 21 | 3277.0 | 45 | 445.0 | 4466.0 |

| Example | Anionic Compound Example | Anionic Compound Grams | Cationic Compound Example | Cationic Compound Grams | Water Grams |
|---------|---------|-------|---------|-------|-------|
| 66 | 22 | 893.0 | 46 | 280.0 | 1257.0 |
| 67 | 23 | 1024.0 | 47 | 308.0 | 1600.0 |
| 68 | 24 | 861.0 | 48 | 336.0 | 1436.0 |
| 69 | 25 | 537.0 | 49 | 574.0 | 1333.0 |
| 70 | 26 | 888.0 | 50 | 770.0 | 1812.0 |
| 71 | 27 | 2679.0 | 51 | 511.0 | 3992.0 |
| 72 | 28 | 593.0 | 52 | 406.9 | 1250.0 |
| 73 | 29 | 3325.0 | 51 | 511.0 | 5754.0 |
| 74 | 30 | 941.0 | 50 | 770.0 | 2053.0 |
| 75 | 31 | 1072.0 | 49 | 574.0 | 1646.0 |
| 76 | 32 | 909.0 | 45 | 445.0 | 1760.0 |

Applications Evaluation

Control Compounds

Stearalkonium Chloride is an excellent conditioning agent having outstanding substantivity to hair. It has detangling properties, improves wet comb when applied after shampooing. The FDA formulation data for 76 reports the use of this material in 78 hair conditioners, eight at less than 0.1%, eighteen at between 0.1 and 1.0% and 52 at between 1 and 5%.

Cetyltrimonium Chloride, or CTAC, is a very substantive conditioner which in addition having a non-greasy feel, improves wet comb and also provides a gloss to the hair. It is classsified as a severe primary eye irritant. Therefore its use concentration is generally at or below 1%.

Eye Irritation

Eye irritation is a major concern in the formulation of personal care products, particularly when working with quats. Primary eye irritation using the protocol outlined in FHSLA 16 CFR 1500.42 The products were tested at 25% actives. The results were as follows:

Cationic Compounds (Not of the Present Invention)

| | |
|---|---|
| Stearalkonium Chloride | 116.5 Severely Irritating |
| Cetyltrimethyl ammonium Chloride | 106.0 Severely Irritating |
| Cetyltriethyl ammonium Chloride | 115.0 Severely Irritating |

Complexes of the Present Invention

| Example | 56 | 8.1  | Minimally Irritating |
|---------|----|------|----------------------|
| Example | 61 | 11.3 | Minimally Irritating |
| Example | 62 | 10.2 | Minimally Irritating |
| Example | 70 | 4.9  | Minimally Irritating |
| Example | 76 | 7.8  | Minimally Irritating |

As the data clearly shows, the irritation potential of the complex is dramatically reduced, when compared to the starting quat.

Typical Formulations

The compounds of the present invention are generally formulated into shampoos, bubble baths and shower gels. The formulations contain water, an anionic surfactant, commonly fatty alcohol sulfates or preferably fatty alcohol ether sulfates having 1 to 4 moles of polyoxyethylene groups present, between 0.01 and 10.0% by weight of the compounds of the present invention, and optionally, dimethicone copolyol, cocamidopropyl betaine, alkanolamids, polysorbates and antimicrobials, like for example Triclosan.

Specific Formulation Examples

CLEAR SOFTENING SHAMPOO B090-CS-1

|    | INGREDIENTS             | PERCENT       |
|----|-------------------------|---------------|
| A. | Deionized Water         | QS to 100.00  |
|    | Sodium Laureth Sulfate  | 30.00         |
|    | Cocamide DEA            | 2.50          |
|    | Cocamidopropyl Betaine  | 7.00          |
|    | Dimethicone Copolyol    | 2.00          |
|    | Silicone Panthenol      | 1.50          |
|    | Example 53              | 6.50          |
| B. | Quaternium-15           | 0.20          |
| C. | Citric Acid 50% Solution| QS            |

PROCEDURE

1. In a suitable container, combine all ingredients together of Phase A with good agitation, mix without aerating. Begin to heat to 70–75° C. When clear and uniform, stop heating and cool to 35–40° C.
2. Add Phase B. Mix well
3. Add Phase C. Adjust pH to 6.3–6.8.

MILK FACIAL SCRUB B095-CS-1

|    | INGREDIENTS             | PERCENT       |
|----|-------------------------|---------------|
| A. | Deionized water         | Qs to 100.00  |
|    | Sodium laureth sulfate  | 30.00         |
|    | Cocamid DEA             | 2.50          |
|    | Cocamidopropyl betaine  | 7.00          |
|    | Dimethicone copolyol    | 1.00          |
|    | Example 55              | 3.00          |
| B. | Chamomile Extract       | 1.00          |
|    | Mallow Extract          | 1.00          |
|    | Cucumber Extract        | 1.00          |
| C. | Jojoba Beads            | 5.00          |
| D. | Germaben II             | 1.00          |
|    | Fragrance               | 0.50          |

PROCEDURES

1. In a suitable container, add water and begin to heat to 70–75° C.
2. Add remaining ingredients of phase A, one at a time.
3. Mix well.
4. Cool to 30–35° C., add phase B mix well.
5. Add phase C, mix without aerating
6. Add phase D, mix until uniform

BODY WASH B092-CS-1

|    | INGREDIENTS                  | PERCENT       |
|----|------------------------------|---------------|
| A. | Deionized Water              | QS to 100.00  |
|    | Sodium Laureth Sulfate       | 30.00         |
|    | Cocamidopropyl Betaine       | 7.00          |
|    | Methylparaben                | 0.15          |
|    | Propylparaben                | 0.05          |
|    | Example 65                   | 1.50          |
|    | Cocamide DEA                 | 3.00          |
|    | Eethylene glycol distearate  | 2.50          |
|    | Dimethicone Copolyol         | 2.00          |
| B. | Imidazolidinyl Urea          | 0.30          |
|    | Cirtric Acid/TEA             | QS            |
| C. | Cucumber Extract             | 0.25          |
|    | Elder Extract                | 0.25          |
|    | Matricaria Extract           | 0.25          |
|    | Ginkgo Extract               | 0.25          |
| D. | Fragrance                    | 0.50          |

PROCEDURE

1. In a suitable container, weigh and add all the ingredients of Phase A one at a time with good agitation
2. Begin to heat to 75–80° C. Mix until uniform
3. Begin to cool to 40–45° C. Add Phase B, then Phase C. Mix well
4. Add Phase D.
5. Mix well. Cool to 35° C.

SKIN CONDITIONING BUBBLE BATH B093-CS-1

|    | INGREDIENTS                                     | PERCENT       |
|----|-------------------------------------------------|---------------|
| A. | Deionized Water                                 | QS to 100.00  |
|    | Decyl Polyglucose (and) Ammonium Laureth Sulfate| 18.00         |
|    | Biosil Basics Cocosil                           | 5.00          |
|    | Cocamidopropyl Betaine                          | 3.00          |
|    | Cocamide DEA                                    | 2.50          |
| B. | Example 53                                      | 5.00          |
| C. | Complex Aligomarin                              | 2.00          |
| D. | Preservative                                    | 1.00          |
| E. | QS Fragrance and Color                          | QS            |

PROCEDURE

1. Combine ingredients in Phase A and heat to 45–50° C. with careful mixing.
2. When all ingredients are melted and uniform, add Phase B. Mix well.
3. Cool to 35° C. Add Phase C while mixing.
4. Add Phase D then Phase E. Mixing carefully.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A process for conditioning hair which comprises contacting the hair with an effective conditioning amount of a complex conforming to the following structure:

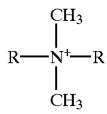

$$R^1-O-C(O)R^2C(O)O^-$$

wherein;

$R^1$ is $CH_3-(CH_2)_n-O-(CH_2CH_2O)_a-(CH_2CH(CH_3)O)_b-(CH_2CH_2O)_c-$;

n is an integers ranging from 7 to 21;

a and c are integers independently ranging from 0 to 20, with the proviso that a+b be greater than 5;

b is an integer ranging from 0 to 20;

$R^2$ is selected from the group consisting of $-CH_2-CH_2-$, $-CH=CH-$, and

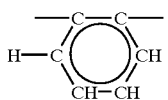

$R^3$ is selected from the group consisting of $CH_3(CH_2)_e-$ and $R^5-C(O)N(H)-(CH_2)_3-$ $R^5$ is $CH_3(CH_2)_f-$ e is an integer from 5 to 21;

f is an integer from 5 to 21;

$R^4$ is selected from the group consisting of $CH_3(CH_2)_g$ g is an integer ranging from 0 to 21 and

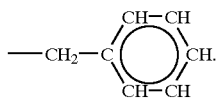

2. A process of claim 1 wherein $R^1$ is $CH_3-(CH_2)_n-O-(CH_2CH_2O)_a-(CH_2CH(CH_3)O)_b-(CH_2CH_2O)_c-$ 3. A process of claim 2 wherein $R^2$ is $-CH_2-CH_2-$.

4. A process of claim 2 wherein $R^2$ is $-CRH=CR-$.

5. A process of claim 2 wherein $R^2$ is

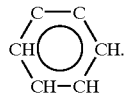

6. A process of claim 3 wherein $R^3$ is alkyl having 8 to 22 carbon atoms.

7. A process of claim 4 wherein e is an integer ranging from 7 to 21.

8. A process of claim 5 wherein e is an integer ranging from 7 to 21.

9. A process of claim 3 wherein $R^3$ is;

$R^5C(O)N(H)-(CH_2)_3-$ $R^5$ is alkyl having 5 to 21 carbon atoms.

10. A process of claim 4 wherein $R^3$ is;

$R5C(O)N(H)-(CH_2)_3-$ $R^5$ is all having 5 to 21 carbon atoms.

11. A process of claim 5 wherein $R^3$ is;

$R^5C(O)N(H)-(CH_2)_3$ $R^5$ is alkyl having 5 to 21 carbon atoms.

12. A process of claim 6 wherein $R^4$ is methyl.
13. A process of claim 7 wherein $R^4$ is methyl.
14. A process of claim 8 wherein $R^4$ is methyl.
15. A process of claim 9 wherein $R^4$ is methyl.
16. A process of claim 10 wherein $R^4$ is methyl.
17. A process of claim 11 wherein $R^4$ is methyl.
18. A process of claim 6 wherein $R^4$ is

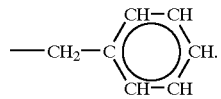

19. A process of claim 7 wherein $R^4$ is

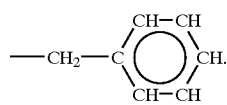

* * * * *